United States Patent [19]
Gombotz et al.

[11] Patent Number: 5,900,238
[45] Date of Patent: * May 4, 1999

[54] VACCINE DELIVERY SYSTEM

[75] Inventors: Wayne R. Gombotz, Kirkland; Siow Fong Wee, Edmonds; William C. Fanslow, III, Federal Way, all of Wash.

[73] Assignee: Immunex Corporation, Seattle, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/508,229

[22] Filed: Jul. 27, 1995

[51] Int. Cl.$^6$ ............................. A61K 39/00; A61K 9/14; A61K 9/51; A61K 45/00
[52] U.S. Cl. ...................... 424/184.1; 424/489; 424/490; 424/496; 424/497; 424/85.2; 424/185.1; 424/192.1; 424/198.1; 424/278.1
[58] Field of Search .............................. 424/184.1, 193.1, 424/278.1, 279.1, 451, 489, 490, 496, 497, 85.2, 185.1, 192.1, 198.1

[56] References Cited

U.S. PATENT DOCUMENTS

| | | | |
|---|---|---|---|
| 4,744,933 | 5/1988 | Rha et al. | 264/4.3 |
| 5,529,777 | 6/1996 | Andrianov et al. | 424/184.1 |
| 5,674,495 | 10/1997 | Bowersock et al. | 424/184.1 |

FOREIGN PATENT DOCUMENTS

| | | |
|---|---|---|
| 0 323 708 | 7/1989 | European Pat. Off. . |
| WO 92/01784 | 2/1992 | WIPO . |

OTHER PUBLICATIONS

Eldridge et al., "Biodegradable Microspheres: Vaccine Delivery System for Oral Immunization", Current Topics in *Microbiology and Immunology* 146: 59–66, 1989.

Eldridge et al., "Biodegradable Microspheres As A Vaccine Delivery System", *Molecular Immunology* 28(3): 287–298, 1991.

Marx et al., "Protection Against Vaginal SIV Transmission with Microencapsulated Vaccine", *Science* 260: 1323–1327, 1993.

Aguado and Lambert, "Controlled–Release Vaccines –Biodegradable Polylactide/Polyglycolide (PL/PG) Microspheres as Antigen Vehicles", *Immunobiology* 184: 113–125, 1992.

Offit et al., "Enhancement of Rotavirus Immunogenicity by Microencapsulation", *Virology* 203: 134–143, 1994.

Bowersock et al., "Evaluation of an Orally Administered Vaccine, Using Hydrogels Containing Bacterial Exotoxins of *Pasteurella haemolytica*, in Cattle", *Am. J. Vet. Res.* 55(4): 502–509, 1994.

Mumper et al., "Calcium–Alginate Beads for the Oral Delivery of Transforming Growth Factor–$\beta_1$ (TGF–$\beta_1$): Stabilization of TGF–$\beta_1$ by the Addition of Polyacrylic Acid Within Acid–Treated Beads", *Journal of Controlled Release* 30: 241–251, 1994.

(List continued on next page.)

*Primary Examiner*—Ponnathapura Achutamurthy
*Attorney, Agent, or Firm*—Patricia Anne Perkins; Janis C. Henry

[57] ABSTRACT

Compositions comprising an immunogenic amount of an antigen encapsulated in a stabilized hydrogel microbead are disclosed. The compositions provide a delivery system for antigens such as vaccines. Also provided are methods of stimulating an immune response comprising administration of the inventive compositions.

18 Claims, 3 Drawing Sheets

OTHER PUBLICATIONS

Puolakkainen et al., "Novel Delivery System for Inducing Quiescence in Intestinal Stem Cells in Rats by Transforming Growth Factor β1", *Gastroenterology* 107: 1319–1326, 1994.

Singh et al., "Controlled Delivery of Diphtheria Toxoid Using Biodegradable Poly (D,L–Lactide) Microcapsules", *Pharmaceutical Research* 8 (7): 958–961, 1991.

Brown et al., "Enhancement by Microencapsulation of Rotavirus–Specific Intestinal Immune Responses in Mice Assessed by Enzyme–Linked Immunospot Assay and Intestinal Fragment Culture", *Journal of Infectious Diseases* 171: 1334–1338, 1995.

Eldridge et al., "Controlled Vaccine Release in the Gut–Associated Lymphoid Tissues. I. Orally Administered Biodegradable Microspheres Target the Peyer's Patches", *Journal of Controlled Release* 11: 205–214, 1990.

Bowersock et al., "Oral Vaccination of Animals Via Hydrogels", *Proceed. Intern. Symp. Control. Rel. Bioact. Mater.* 21: 79–80, 1994.

VACCINE DELIVERY SYSTEM

FIELD OF THE INVENTION

The invention relates generally to the field of vaccine compositions, and more specifically to vaccine compositions suitable for immunization via mucosal tissue. The invention also pertains to methods of eliciting an immune response.

BACKGROUND OF THE INVENTION

Most vaccines licensed for use in humans are administered parenterally, which is an effective route for generating a systemic immune response. However, parenteral immunization produces predominantly IgM and IgG on mucosal surfaces, where most pathogenic or opportunistic organisms initiate infection, and is not very effective in protecting individuals from air borne or mucosal-related infectious diseases (Formal et al., *Proc. Soc. Exp. Biol. Med.* 125:347, 1967; Mestecky, J. *J. Clin. Immunol.* 7:265, 1987). Protective, antigen specific secretory IgA (sIgA) antibodies are only efficiently induced when antigen is administered to the mucosal sites (McGhee, J. R. and Mestecky, *J. Infec. Dis. Clin. North. Amer.* 4:315, 1990).

Several studies in the area of mucosal immunization have utilized live, attenuated viruses or bacteria as the immunogen (Treanor et al., *Ann. Intern. Med.* 117:625, 1992; Clements et al., *Vaccine* 6:269, 1988). In these studies, administration of the attenuated microbes resulted in effective protection and induced both local and systemic immunity. Intranasal administration of particulate antigens has also been described (Peter et al. *Infec. and Immun.* 40:1092, 1983). However, administration of soluble antigens to mucosal surfaces has been hampered by the lack of appropriate delivery vehicles or soluble adjuvants that stimulate mucosal IgA secretion.

New delivery methods, including synthetic or naturally occurring polymers, and liposome preparations, have been investigated as means for the controlled and/or targeted delivery of soluble immunogens. Abraham (*Vaccine* 10:461, 1992) reported that the intranasal administration of liposome-contained antigen reduced the dose of antigen required to elicit a mucosal immune response. Almeida and co-workers (*J. Pharm. Pharmacol.* 45:198, 1993) reported similar findings using poly (L-lactic acid) microspheres. Several other types of microspheres have also been investigated for use as vaccine antigen carriers. In one study, uptake by gut-associated lymphoid tissue (GALT), a necessary first step in generating a protective immune response, was dependent upon the type and diameter of the microparticle (Eldridge et al., *J. Controlled Release* 11:205, 1990). Other hydrogels have also been used for oral vaccination of animals (Bowerstock et al., *Pro. Intern. Symp. Control. Rel. Bioact. Mater.* 21:79. 1994).

Alginate is a pH-sensitive, biodegradable material that forms a gel matrix in the presence of divalent cations, and has been used in microencapsulation technology for entrapment of antibodies, subcellular organelles, cells, bacteria, nucleic acids and proteins (Tai et al., *FASEB.* 7:1061, 1993; Smidsrod, O. and Skjak-Braek, G. *TIBTECH* 8:71, 1990; Smith, T. J., *BioPharm.* 7:54, 1994; Duff, R. G., *TIBTECH* 3:167, 1985; Downs, et al., *J. Cell Physiol.,* 152:422, 1992; Puolakkainen et al., *Gastroenterology* 107:1319, 1994; Soon-Shiong et al., *Lancet* 343:950, 1994), and for other pharmaceutical agents (Stockwell, et al., *J. Controlled Release,* 3:167, 1986; Segi, et al., *Chem. Pharm. Bull.,* 37:3092, 1989; Bahkoo, et al., *Pro. Int. Symp. Controlled Release Bio. Mater.* 18:441, 1991).

Recent efforts in vaccine design have focused on improved vaccine delivery systems (Langer, R. *Science,* 249: 1527, 1990). A vaccine delivery system that can provide both priming and boosting administrations in a single dose would be very beneficial. Additionally, a system that could protect proteins and other agents from hostile environments, i.e., the low pH and battery of proteolytic or digestive enzymes present in the stomach, would facilitate development of effective vaccines. There is also a need in the art for vaccine delivery systems that utilize only small amounts of antigen, to allow simultaneous administration of more than one immunogen. Such a delivery system for soluble vaccine antigens would also allow self-administration, and would enhance the ability of health professionals to control or eliminate infectious diseases.

BRIEF DESCRIPTION OF THE DRAWINGS

FIG. 1 illustrates the induction of IgG1 antibodies to OVA after a single intranasal instillation of OVA encapsulated in poly-L-lysine (FIG. 1A) or polyhistidine (FIG. 1B) coated alginate beads, as described in Example 5.

SUMMARY OF THE INVENTION

The present invention provides a composition comprising an immunogenic amount of an antigen encapsulated in a hydrogel microbead. The microbead may be stabilized, for example, by the addition of a poly-cation coating. Optionally, the bead may have an additional alginate coating on the poly-cation. The antigen is a molecule comprising one or more epitopes against which an immune response can be developed. The antigen can be a protein, glycoprotein, carbohydrate or other type of molecule that can stimulate an immune response, and is used in a purified or partially purified form.

In the compositions of the invention, the active ingredient (the antigen) is typically provided in amounts of about 0.25 percent of the dry weight of the total composition, to about 50 percent of the dry weight of the total composition. Preferred ranges of active ingredient are from about one (1) percent of the dry weight to about 25 percent of the dry weight. The active ingredient may consist of a single type of antigen, or may comprise two or more antigens. Immunoregulatory molecules may also be included, to enhance a desired immune response.

Typical alginate solutions used to prepare the beads can range from about 0.1 weight-to-volume percent to about 5 weight-to-volume percent. Preferred alginate solutions comprise about 0.5 weight-to-volume percent to about 2 weight-to-volume percent. Microbeads may be prepared using an atomizing device (air or ultrasonic atomization devices), or water/oil emulsion techniques. Useful cross-linking solutions include solutions of a divalent cation such as calcium chloride, barium chloride or strontium nitrate; preferred solutions are from about 0.5% to about 2% by weight of the divalent cation, with the most preferred concentration being 0.5%.

DETAILED DESCRIPTION OF THE INVENTION

The different types and levels of OVA-specific and Pn14-specific antibodies in mouse serum were measured and compared when the encapsulated antigens in alginate microbeads were delivered subcutaneously or intranasally. As little as 3 μg of antigen was shown to induce a primary response as early as 14 days after a single immunization. Levels of specific antibodies induced by intranasal instillation were comparable to or better than, in the case of IgA and IgG2,b those induced by subcutaneous administration. IgE was not detected in these studies. Antigen-specific antibody was detected in mice that had been vaccinated by intranasal instillation over a period of 143 days, indicating that a single dose vaccine administration can be achieved with polyhistidine coated beads. The results presented herein demonstrate that an effective immune response is induced when soluble antigens are encapsulated in a hydrogel matrix, and administered to an individual in need of immunization. Moreover, an adjuvant is not required to generate this immune response.

The protective immune response

An immune response to a pathogen can be classified broadly as either being cell-mediated (cellular immunity) or antibody mediated (humoral immunity). In cellular immunity, activated macrophages and cytotoxic lymphocytes carry out elimination of the pathogen. Humoral immunity, in contrast, operates primarily through antibody production. It is currently believed that these two arms of the immune response are regulated by distinct subsets of helper T ($T_H$) cells which secrete specific arrays of cytokines (reviewed in i Immunological Reviews 123, 1991).

Type 1 $T_H$ cells ($T_H1$ cells) mediate delayed type hypersensitivity (DTH), and secrete Interferon-γ (IFN-γ) and Interleukin-2 (IL-2), while Type 2 $T_H$ cells ($T_H2$ cells) secrete primarily Interleukins 4, 5 and 10 (IL-4, IL-5 and IL-10, respectively) and provide B cell help. Development of the immune response along either $T_H1$ or $T_H2$ pathway is often apparent early in an infection, and appears to be governed by the type of organism causing the infection (Scott and Kaufmann, Immunol. Today 12:346, 1991), and by the genetic makeup of the infected host. Failure to resolve disease or development of immunopathology can result when the immune response proceeds inappropriately.

The immune response may be manipulated toward either a $T_H1$, cell mediated response, or $T_H2$, antibody mediated response, by the appropriate administration of cytokines, or cytokine antagonists. For example, administration of IFN-γ or an antibody that neutralizes IL-4 would enhance a $T_H1$ response, whereas administration of IL-10 or a molecule that inhibited the action of IFN-γ would stimulate a $T_H2$ response. This ability to manipulate the immune response provides a useful tool not only in infectious disease, but in inflammatory and allergic diseases as well (see, for example, Powrie and Coffman, Immunol. Today 14:270, 1993).

The mucosal immune system

Skin and the mucous membranes of the respiratory, intestinal and genitourinary tracts are the first line of defense against infection by pathogenic or opportunistic organisms. The mucous membranes exhibit a sophisticated immune system (the mucosal immune system) that is largely distinct from the blood-born (or systemic) immune system, and can be anatomically and functionally divided into inductive tissues, where antigen is encountered and the initial immune response is induced, and effector tissues, where secretory IgA (sIgA) is produced (Bernstein et al., in Handbook of mucosal immunology, Ogra, P. L. ed., San Diego, Academic Press Inc., 1994, page 625).

The inductive sites consist of specialized lymphoreticular tissues referred to as bronchus-associated or nasal-associated lymphatic tissue (BALT or NALT respectively), and gut-associated lymphatic tissue (GALT). The Peyer's patches of the intestine are important inductive sites in the GALT, and give rise to both cell-mediated and humoral immunity (McGhee et al., Vaccine, 10:75, 1992; Mestecky, J. and McGhee, JR., Advances in Immunol. 40:153, 1987). Specialized cells known as microfold, or M, cells transport intact antigen from the lumen of the intestinal tract to the basolateral surface where the antigen can interact with the lymphoreticular cells. The palatine and nasopharyngeal tonsils are important inductive sites for the BALT, and like Peyer's patches, are structurally organized lymphoid tissue containing both B and T cells, and provide an environment for induction of the immune response (Bienenstock, J., in Immunology of the lung and upper respiratory tract. Bienenstock, J. ed., McGraw-Hill, New York, 1980, page 96).

Effector sites include the lamina propria of the respiratory, intestinal and genitourinary tracts, and glands such as the salivary, mammary and lachrymal glands (Staats et al., Current Opinion in Immunol. 6:572, 1994). Antigen-specific T and B cells from the inductive tissues travel via the efferent lymphatic system, through the thoracic duct, to the systemic circulation. From there, they reach the effector sites, from which they can mount both a cytotoxic lymphocyte (CTL) response, and the sIgA response that is the hallmark of the mucosal immune system. Macrophages, eosinophils and mast cells are also present in effector tissues.

Vaccines and disease

Immunization is a centuries old, and highly effective, means of inducing a protective immune response against pathogens in order to prevent or ameliorate disease. The vaccines that have been used for such induction are generally live, attenuated microorganisms, or preparations of killed organisms or fractions thereof. Live, attenuated vaccines are generally thought to more closely mimic the immune response that occurs with a natural infection than do those prepared from killed microbes or non-infective preparations derived from pathogens (i.e., toxoids, recombinant protein vaccines). However, attenuated vaccines also present a risk of reversion to pathogenicity, and can cause illness, especially in immunocompromised individuals.

Along with improved sanitation, immunization has been the most efficient means of preventing death or disability from numerous infectious diseases in humans and in other animals. Vaccination of susceptible populations has been responsible for eliminating small pox world wide, and for drastic decreases in the occurrence of such diseases as diphtheria, pertussis, and paralytic polio in the developed nations. Numerous vaccines are licensed for administration to humans, including live virus vaccines for certain adenoviruses, measles, mumps and rubella viruses, and poliovirus, diphtheria and tetanus toxoid vaccines, and Haemophilus b and meningococcal polysaccharide vaccines (Hinman et al., in Principles and Practice of Infectious Diseases, 3rd edition; G. L. Mandell, R. G. Douglas and J. E. Bennett, eds, Churchill Livingstone Inc., NY, N.Y.; 2320–2333; Table 2).

Despite the successes achieved with these vaccines, however, there are still numerous challenges in the field (*Science* 265:1371; 1994). HIV infection is a public health problem in both developed and developing nations; there has been little progress in developing an effective vaccine against this virus despite significant research efforts in this area. Malaria and tuberculosis represent significant public health challenges in the developing world, with high morbidity and mortality rates, and problematic treatment regimes. Respiratory syncytial virus (RSV) and pneumococcal disease pose similar difficulties in the developed world.

Even for diseases for which there are effective vaccines available, maintaining an sufficient rate of immunization in susceptible populations presents a public health challenge. Many children in the United States are not vaccinated for common childhood diseases such as diphtheria and pertussis. Adults may not receive necessary boosting immunizations for tetanus or other diseases. Parenteral routes of administration, the numbers of different vaccinations required and the need for, and frequency of, booster immunizations all impede efforts to achieve patient compliance with vaccine programs. Developing countries also face additional challenges in trying to store and administer vaccines.

Several aspects of vaccine preparation and administration have been investigated. Abraham (*Vaccine* 10:461, 1992) reported that the intranasal administration of liposome-contained antigen required only about 1/30th of the dose required for intragastric administration to elicit an immune response. Almeida and co-workers (*J. Pharm. Pharmacol.* 45:198, 1993) reported similar findings using tetanus toxoid encapsulated in poly (L-lactic acid) microspheres. In this study, repeated administration of higher doses (60 $\mu$g of tetanus toxoid) was required to elicit a primary immune response. In one study, uptake of encapsulated antigen by gut-associated lymphoid tissue (GALT), a necessary first step in generating a protective immune response, was dependent upon the type and diameter of the microparticle (Eldridge et al., *J. Controlled Release* 11:205, 1990).

Encapsulation of antigen preparations can result in the sustained release of the antigen subsequent to administration. The disadvantage associated with a long period of release is that under some circumstances, pulsative release could potentially lead to the induction of tolerance to the antigen administered. Other reactions such as anaphylactic shock may also occur in certain population of individuals. Thus, it is important to design a delivery system that only releases optimal amounts of the antigen for the appropriate amount of time.

Alginate and similar bioadhesive hydrogels

Alginate is a linear polysaccharide extracted from red-brown seaweed, which contains repeating units of 1,4 linked $\alpha$-L-guluronic acid and $\beta$-D-mannuronic acid (Smidsrod, O. and Haug, A. *Acta Chem. Scand* 22:1989, 1968; Smidsrod et al. *Acta. Chem. Scand* 26:2563, 1972). In the presence of divalent cations, sodium alginate spontaneously forms a gel matrix as a result of ionic cross-linking of the guluronic acid residues by the cations. Various forms of alginate (typically 60% 1,4-linked-$\beta$-D-mannuronic acid and 40% $\alpha$-L-guluronic acid; or 30% 1,4-linked-$\beta$-D-mannuronic acid and 70% a-L-guluronic acid) are available commercially.

Because of its ability to form a gel matrix when associated with divalent cations, alginate has been used in microencapsulation technology for entrapment of antibodies, subcellular organelles, cells, bacteria, nucleic acids and proteins (Tai et al., *FASEB*. 7:1061, 1993; Smidsrod, O. and Skjak-Braek, G. *TIBTECH* 8:71, 1990; Smith, T. J., *BioPharm.* 7:54, 1994; Duff, R. G., *TIBTECH* 3:167, 1985; Downs, et al., *J. Cell Physiol.,* 152:422, 1992; Puolakkainen et al., *Gastroenterology* 107:1319, 1994), and has recently been approved for use in human clinical trials by the U.S. Food and Drug Administration. In this study, alginate-encapsulated pancreatic islet cells were successfully placed in the abdominal cavity of insulin-dependent diabetes mellitus patients (Soon-Shiong et al., *Lancet* 343:950, 1994).

Examples of other pharmaceutical agents that have been combined with alginate include those described by Stockwell, et al., *J. Controlled Release,* 3:167–175 (1986) wherein sodium alginate delivery systems for the cationic drugs caffeine, sodium salicylate and chlorpheniramine are presented. Segi, et al., *Chem. Pharm. Bull.,* 37:3092–3095 (1989) describe the cationic drug, propanolol, and its interaction with alginate gel beads. Another cationic drug, theophylline, was examined with alginate gel beads by Bahkoo, et al., *Pro. Int. Symp. Controlled Release Bio. Mater.* 18:441–442 (1991).

Alginate possesses several features which make it a promising polymer candidate as a controlled release matrix. It has been described as having mucoadhesive property (Chickering et al., *Pro. Int. Synp. Cont. Rel. Bioact. Mater.* 19:88, 1992) which enhances its interaction with the mucous membrane lining of the respiratory or gastrointestinal tract. This may increase the biological effectiveness of an encapsulated drug by increasing its absorption, or enhance the immunogenicity of an encapsulated soluble antigen by increasing antigen delivery to inductive sites of mucosal immunity. An alginate encapsulation matrix can also protect proteins and other agents from hostile environments, i.e., the low pH and battery of proteolytic or digestive enzymes present in the stomach. Additionally, alginate is non-toxic when taken orally, and is both bioacceptable and biodegradable.

Moreover, the encapsulation procedure used in preparing the inventive antigen-containing alginate microbeads is a very mild and completely aqueous process which is ideal for the encapsulation of labile proteins. Most such procedures involve mixing together a solution of the antigen of interest and a solution of alginate under physiological conditions, then using divalent cations to form the alginate gel matrix.

Additional modifications may be made to the microbeads to enhance various characteristics. For example, certain poly-cations have been used to form an outer coating on alginate microbeads to increase the mechanical strength and the integrity of the microbeads (Sun et al. In *Advances in Drug Delivery Systems,* Kim, S. W. and Anderson, B. (Eds), Elsevier, Amsterdam, 1986, page 137), and decrease the release rate of the incorporated material from the bead. Poly-L-lysine has been the conventional poly-cation used in the outer coating of alginate beads (Lim et al., *Appl. Biochem. Biotech.* 10:81, 1984). Those of skill in the art will recognize that other methods to increase the strength and integrity of alginate microbeads, or reduce the release rate, are also useful in the inventive compositions.

Bioadhesive components, such as polyacrylic acid or lectin, may be added to alginate to enhance the bioadhesiveness of the inventive compositions. Polyacrylic acid and other anionic additives may also be used to shield positively-charged molecules from ionized alginate molecules, enhancing their release kinetics and stabilizing biological activity, for example as described by Mumper et al. (*J. Controlled Release* 30:241, 1994). Furthermore, other bioadhesive hydrogels will also be useful in the inventive compositions. Examples of such hydrogels include cross-linked pectin, gelatin, collagen, albumin, chitosan, cellulose and its derivatives, hyaluronic acid and its ester derivatives, polyvinyl alcohol, polymethacrylic acid, starches and dextrans, polyvinyl pyrrolidone, pluronic polyols and polyethylene oxide. The skilled artisan can select the appropriate hydrogel and modify it as described herein or as is known in the art to prepare useful vaccine compositions.

Preparation of compositions

The present invention provides compositions comprising an amount of an antigen effective to stimulate an immune response, encapsulated in a hydrogel microbead. The antigen can be any type of molecule against which it is desired to elicit an immune response, and comprises one or more specific epitopes. In the compositions of the invention, the active ingredient (the antigen) is typically provided in amounts of about 0.1 percent of the dry weight of the total composition, to about 50 percent of the dry weight of the total composition. Preferred ranges of active ingredient are from about one (1) percent of the dry weight to about 25 percent of the dry weight.

The active ingredient can comprise one or more proteins or other molecules. For example, the inventive vaccine compositions can consist of two or more different antigens, in the presence or absence of additional immunoregulatory molecules. Such mixtures can be obtained by preparing a solution that contains all the desired components (i.e., two or more antigens, or an antigen and a cytokine, and combinations thereof), and using the solution as described herein to prepare microbeads in which the heterologous molecules are present in the individual beads. Alternatively, the different molecules can be encapsulated separately, and mixtures obtained by mixing the various types of microbeads in the desired proportions.

A preferred hydrogel is alginate. Typical alginate stock solutions used to prepare the beads can range from about 0.1 weight-to-volume percent to about 5 weight-to-volume percent. Preferred alginate solutions comprise about 0.5 weight-to-volume percent to about 2 weight-to-volume percent, with 2 percent being most preferred. When the alginate stock solutions are mixed with the molecules to be encapsulated, the final concentration of alginate will approximately one-half that of the stock solution. Other hydrogels can also be used. Suitable conditions for their use are determined by routine experimentation.

Microbeads are prepared, for example, by spraying the antigen/alginate mixture through a single-orifice air-atomizing device manufactured by TurboSonics, Waterloo, Ontario, Canada. The nozzle of the device has at least one orifice with a diameter of from 0.5 mm to about 2 mm. Most preferably, the orifice is 1.0 mm. The spray angle is from about 10 to about 20°, most preferably from about 12 to about 15°. Optionally, the device is also equipped with an inlet from which $N_2$ gas can be introduced at a constant pressure, from about 20 to about 40 psi, most preferably at 25 psi. A two-orifice nozzle can be used as well. The divalent cross-linking solution is sprayed from the second orifice, and will partially cross-link the antigen/alginate droplets that are emitted from the first orifice. Other suitable devices include ultrasonic atomization nozzles. Similar results can be obtained by using a water/oil emulsion technique substantially as described by Wan et al., *J. Microencapsulation* 9:309, 1992, or Maysinger et al., *Neuroscience Letters* 140:71, 1992, or by using other methods or devices useful for micronizing solutions.

The antigen/alginate mixture is sprayed at an infusion rate of from about 2 to about 3 ml/min., most preferably at 2.2 ml/min. for a 10 ml sample, into a vessel containing crosslinking solution. Exemplary cross-linking solutions include solutions of divalent cations such as calcium chloride, barium chloride or strontium nitrate; a preferred solution is from about 0.5% to about 2% by weight of the divalent cation, with the most preferred concentration being 0.5%. Optimally, the crosslinking solution is stirred gently, for example, with a magnetic stir bar, to assure even distribution of the antigen/alginate mixture. The distance between the surface of the nozzle and the crosslinking solution is one factor in controlling bead size.

The microbeads that form upon contact of the alginate/antigen mixture are allowed to cure for from about 5 to about 30 minutes, preferably for 10 minutes. If desired, the curing period is followed by addition of a solution of poly-cation. Preferred poly-cations are poly-L-lysine, polyhistidine, polyarginine and polyethyleneimine; polyhistidine is most preferred. After an additional 5 to 30 minutes (preferably 10 minutes), the microbeads are then treated to remove clumps of alginate that may form during the initial stage of the fabrication process. An exemplary treatment is sieving, for example, through a particle sieve having pores of a desired size, preferably from about 1 $\mu$m to about 150 $\mu$m. Most preferably, the pores are less than about about 106 $\mu$m. The sieved beads comprise a population of microbeads having a range of diameters that are smaller that the pore size of the sieve. Average bead size can be determined as described herein, and the appropriate size of beads for a particular usage selected. The treated microbeads are then washed, and the amount of incorporated antigen can be determined, for example, by determining the nitrogen content of the protein encapsulated in the beads.

A final coating of an outer alginate layer may be added to the microbeads by incubating them in a solution of alginate. The solution is from about 0.01% to about 0.05% alginate; most preferably, the solution is 0.03% alginate. The coated beads are washed, and resuspended in a biologically acceptable diluent, for example 0.9% NaCl or 0.5% $CaCl_2$, and stored, preferably at 4° C. The beads can also be lyophilized or frozen for long-term storage. Suitable conditions, including excipients and stabilizing agents, for such long-term storage will depend on the characteristics of the molecules that are encapsulated in the beads.

The diameter of the microbeads is controlled by the diameter of the nozzle orifice used, the pressure of the gas introduced into the nozzle, and the distance from the nozzle to the crosslinking solution. Other parameters can be controlled to determine bead size when water/oil emulsion techniques are used. Bead diameter can be determined, for example, by using a Malvern particle analyzer. Beads having a diameter of from about 0.5 $\mu$m to about 100 $\mu$m are suitable for use in the inventive compositions. Most preferably for administration of an antigen to the respiratory mucosa, the diameter is less than about 100 $\mu$m, with an average bead size of between about 30 and about 50 $\mu$m, although microbeads with diameters greater than 100 $\mu$m can be used for other clinical indications. For oral administration of an antigen, beads that are small enough to allow uptake by M cells are preferred, namely, beads having a diameter that is on average less than about 10 $\mu$m, with a preferred range of from about 5 $\mu$m to about 15 $\mu$m. Microbeads with diameters greater than about 10 $\mu$m can be used for other clinical indications. Larger beads can also be prepared, and may be useful for other routes of administration. Heterogeneous mixtures of beads having diameters in these ranges are also acceptable for the invention.

The inventive compositions may also comprise ancillary molecules, such as a suitable diluent or carrier, buffers, antioxidants such as ascorbic acid, low molecular weight (less than about 10 residues) polypeptides, preservatives, proteins, amino acids, carbohydrates including glucose, sucrose or dextrins, glutathione and other stabilizers and excipients. Neutral buffered saline or normal saline are exemplary appropriate diluents. The inventive compositions may also be formulated as lyophilizates using appropriate excipient solutions (e.g., sucrose) as diluents. Such ancillary molecules will be nontoxic to recipients at the dosages and concentrations employed, and will depend on the route of administration chosen for the composition.

Administration of alginate/antigen compositions

The inventive compositions are administered to an individual in need of immunization by a route that facilitates exposure of the mucosal immune system to the antigen-containing beads. The inventive compositions can also be administered parenterally, by various routes that are known in the art. Individuals in need of immunization include children or naive adults for whom it is desired to reduce or eliminate the chances of acquiring an infectious disease. The inventive compositions will also be useful in allergic desensitization, since they do not induce an IgE response.

The route of administration will depend on the condition being treated. Thus, for example, the inventive compositions are administered intranasally, intratracheally, directly into the lungs, orally, vaginally or rectally. For administration to the respiratory tract, the compositions may be administered as droplets of liquid suspension, or as aerosols of the microparticles. The aerosols can be generated by conventional nebulizers such as a jet nebulizer or an ultrasonic nebulizer. For other routes of administration, the microbeads can be administered in a solution, gel or cream, in the form of a capsule, or by any other suitable means, including by injection or surgical implantation.

The use of the inventive compositions in conjunction with soluble cytokine receptors, cytokines, or other immunoregulatory molecules is also contemplated. The immunoregulatory molecules may be co-administered with the inventive compositions, or may be separately administered. Optionally, such immunoregulatory molecules are incorporated into alginate beads in a manner similar to that described herein for encapsulation of antigens, either alone or in conjunction with the antigen(s).

Exemplary immunoregulatory molecules include granulocyte-macrophage colony stimulating factor (GM-CSF), such as that described in U.S. Pat. No. 5,393,870; a fusion protein comprising GM-CSF and Interleukin-3 (IL-3), described in U.S. Pat. No. 5,073,627; CD40 ligand, described in U.S. Ser. No. 08/249,189, filed May 24, 1994; Interleukin-15, described in U.S. Ser. No. 08/393,305, filed Feb. 22, 1995; Interleukin-16, described in U.S. Ser. No. 08/410,535, filed Mar. 23, 1995; and antagonists of the interaction of CD30 and CD30 ligand, described in U.S. Ser. No. 98/399,415, filed Mar. 2, 1995. Fusion proteins comprising antigen and an immunoregulatory molecule will also be useful in the inventive compositions. For example, U.S. Ser. No. 08/271,875, filed Jul. 7, 1994, discloses fusion proteins of GM-CSF and antigens. Other cytokines may also be used to prepare such antigen fusion proteins.

Other molecules known in the art to enhance a protective immune response include Interleukin-12, Interleukin-4, Interleukin-5, Interleukin-7 and other cytokines (see, for example, Schrader, J. W. *Mol. Immunol.* 28:295, 1991). Smaller, immunomodulatory peptides derived from such molecules will also be useful in the instant compositions (Nencioni et al., *J. Immunol.* 139:800; 1987) The molecules chosen will depend upon the type of immune response that is desired (i.e., $T_H1$ versus $T_H2$. Adjuvants (molecules that stimulate the immune system, usually by up-regulating endogenous cytokines) may also be used in conjunction with the inventive vaccine compositions, although they are not required to elicit an immune response when the inventive delivery system is used. Many useful adjuvants are described by Vogel and Powell in *A Compendium Of Vaccine Adjuvants And Excipients* (in *Vaccine Design*, M. F. Powel and M. J. Newman, Eds. Pharmaceutical Biotechnology Series, Plenum Publishing Corporation, NY, N.Y.; 1994).

Appropriate dosages for stimulating an immune response can be determined in animals models that are known in the art, and in clinical trials on humans. The amount and frequency of administration will depend, of course, on such factors as the nature of the antigen, the route of administration, the desired response (for example, $T_H1$ versus $T_H2$), the condition of the patient, and so forth. Those of skill in the art are able to determine the appropriate parameters through routine experimentation.

The relevant disclosures of all references cited herein are specifically incorporated by reference. The following examples are intended to illustrate particular embodiments, and not limit the scope, of the invention.

EXAMPLE 1

Fabrication of Alginate Microbeads

Low viscosity alginate from the stipes of *Laminaria hyperborea* (LF 10/60) was obtained from Pronova Biopolymers, Inc. (Portsmouth, N.H.; 30% 1,4-linked-β-D-mannuronic acid and 70% a-L-guluronic acid). A 2% sodium-alginate solution was prepared in distilled water, stirred overnight and filtered through a 0.45 micron filtration unit. The resulting alginate solution was diluted 1:1 with five ml of antigen solution (either 20 mg/ml of ovalbumin, obtained from Sigma, St. Louis, Mo.; or 100 μg/ml of Pn14, a glycoprotein conjugate of 14-valent synthetic polysaccharides from different *Streptococcus pneumoniae* serotypes conjugated to a diphtheria toxin mutein, CRM197; obtained from Lederle-Praxis Biologicals, Rochester, N.Y., and similar to conjugates described in Bixler et al., *Adv. Exp. Med. Biol.* 251:175; 1989), prepared in distilled water. The antigen/alginate mixture was then taken up in a 10-ml Becton-Dickinson plastic syringe and loaded onto a syringe pump (Sage Instruments; distributed by Cole-Parmer, Niles, Ill.).

Microbeads were prepared by spraying the mixture through a glass enclosed air-atomizing device (TurboSonics, Waterloo, Ontario, Canada), which consisted of a nozzle with a single 1.0 mm diameter orifice and a spray angle of 12–15°, and was also equipped with an inlet in which $N_2$ gas at a constant pressure of 25 psi was set. The mixture was sprayed at an infusion rate of 2.2 ml/min. into a vessel containing 400 ml of cross-linking solution (0.5% strontium nitrate; Spectrum, Santa Clara, Calif.) which was stirred gently at 300 rpm with a magnetic stir bar. The distance between the surface of the nozzle and the crosslinking solution was fixed at 14 inches. Encapsulated antigen (ovalbumin or Pn14) was formed upon hitting the surface of the crosslinking solution. The microbeads formed at the end of this stage were termed uncoated beads.

The microbeads were allowed to cure for an additional 10 minutes before addition of a solution of either poly-L-lysine or polyhistidine (both obtained from Sigma, St. Louis Mo.) as described in example 5 below. The solution was stirred for a further 10 minutes, then sieved through a <106 micron in diameter particle sieve (Tyler, Inc., Ohio) to remove clumps of alginate formed during the initial stage (first 10 seconds) of the fabrication process. The sieved solution was then aliquoted into 50-ml conical tubes and centrifuged at 1800 rpm in a Sorvall P5000 for 10 minutes to collect the microbeads. The microbeads were pooled into one 50-ml conical tube, washed once with distilled water, and resuspended.

Alginate solution (0.03% w/v) was added to the microbead suspension, and the resulting mixture was incubated for 10 minutes for the final coating of an outer alginate layer. The suspension was then centrifuged at 1800 rpm, washed once with distilled water and subjected to another centrifugation. The microbeads were resuspended and stored in 0.9% NaCl solution at 4° C. at a concentration of 0.1 mg/ml. The microbeads formed at this final stage were termed coated beads.

The distribution of the diameters of the microbeads produced by the atomizer was determined using a Malvern particle analyzer. Ninety percent (90%) of the microbeads had a diameter of $\leq 106$ microns and the remaining 10% of the beads population had a diameter of $\leq 15$ microns. The median diameter of the microbeads was 41 microns. This heterogeneous population of beads was used in the Examples described herein. Antigen loading was determined by nitrogen analysis (performed by Huffman Labs, Boulder, Colo.) and ranged from 0.51% to 1.0%.

EXAMPLE 2

Intranasal Administration of OVA

Female BALB/c mice (8–12 weeks of age) were purchased from Charles River Laboratories, Inc (Stone Ridge, N.Y.) and maintained under specific pathogen-free conditions. On Day 0 (priming), 10 μg of ovalbumin (OVA), alone or in complete Freund's adjuvant (CFA) was administered subcutaneously (S.Q.) with a 1 cc-syringe fitted with a 25 gauge needle, or by intranasal (I.N.) instillation (3.5 μg of encapsulated OVA in 35 μl) as droplets with Gilson micropipettes, as described below. This procedure was repeated at day 14 (boosting); incomplete Freund's adjuvant (IFA) was used for the control mice that were immunized subcutaneously. For most experiments, mice were lightly anesthetized intraperitoneally with a mixture of ketamine (Fort Dodge Laboratories, Fort Dodge, Iowa.) and zylazine (Miles Inc., Shawnee Mission, Kans.) before each intranasal administration. Subsequent analysis indicated that anesthesia (or lack thereof) did not affect the immune response. Blood was collected from immunized mice by retroorbital venous puncture at day 14 and day 21, and the isolated serum was tested for the presence of OVA-specific subclass antibodies as described in Example 4.

The following microbead administrations were performed: (1) OVA in saline (without microbeads); (2) a mixture of OVA and empty poly-L-lysine coated beads; (3) empty poly-L-lysine coated alginate microbeads; (4) OVA in poly-L-lysine coated alginate microbeads; and (5) OVA in non-coated alginate microbeads. Results of testing serum at day 14 after a first immunization (primary response) are shown in Table 1.

TABLE 1

Ova-specific IgG antibody titer at day 14

| Antigen form | Serum OVA-specific IgG endpoint titer (reciprocal dilution) |
|---|---|
| OVA | <50 |
| Co-administration of OVA and empty coated beads | 50 |
| Empty coated beads | <50 |
| OVA in coated beads | 10,000 |
| OVA in non-coated beads | <50 |

The primary serum IgG responses elicited in the mouse were comparable for both the subcutaneous and intranasal administrations. Moreover, intranasal administration of only 0.1 μg of encapsulated OVA was able to induce a low but detectable level of OVA-specific IgG at day 14. Subsequent secondary boosting with 0.1 μg gave an IgG level comparable to the secondary response obtained from mice that had been administered 3.5 μg of encapsulated OVA during the primary immunization.

The results indicated that OVA administered intranasally in saline and OVA released from non-coated beads or administration of empty poly-L-lysine coated beads alone did not elicit OVA-specific antibody formation. The co-administration of OVA and empty poly-L-lysine coated beads resulted in a low level of antigen-specific antibodies, which could be due to non-specific absorption of OVA to the outer surface of the alginate beads. Only OVA encapsulated and released from poly-L-lysine coated beads showed an OVA IgG antibody titer of 10,000. The elicitation of only low levels of antibody by co-administering OVA and empty microbeads indicated that the alginate microbeads did not act as an adjuvant.

A secondary challenge at day 14 resulted in an increase in the antibody titers at day 21 in both methods of administrations. Both intranasal and subcutaneous administration of OVA resulted in an end-point IgG titer of >100,000. OVA-specific IgA and IgG2b levels measured after the secondary responses showed that higher levels of these antibody subclasses were obtained from animals that were immunized intranasally. In both routes administration, IgE was not detected in the absence of adjuvant (CFA/IFA). The relative levels of the different isotypes of OVA-specific antibodies are shown in Table 2 below. In this table, +++ represents an approximate endpoint titer of >10,000; ++ is an endpoint titer of <10,000 and >1000; + indicates an endpoint titer of <1,000; and −means that no antibody was detected at a dilution of as low as 1:50.

TABLE 2

Comparison of OVA-specific secondary responses by isotype

| OVA-specific Isotype | OVA-alginate beads | | CFA/IFA-OVA emulsion |
|---|---|---|---|
| | S.Q. | I.N. | S.Q. |
| IgM | + | + | + |
| IgG$_1$ | +++ | +++ | +++ |
| IgG$_{2a}$ | + | + | +++ |
| IgG$_{2b}$ | + | ++ | + |
| IgA | + | ++ | + |
| IgE | − | − | + |

Most isotypes were present in the serum from mice that were immunized either intranasally or subcutaneously. The level of OVA-specific antibodies induced in the serum by intranasal administration was comparable to that induced by subcutaneous administration of OVA for IgM, IgG1, and IgG2a. Among the various IgG subclasses obtained, IgG1 was the dominant species observed. Intranasal administration induced higher levels of IgG2b and IgA than did subcutaneous injection.

This study demonstrated that intranasal administration of encapsulated OVA can induce antibody responses which are comparable to those induced by using other routes of administration. Serum IgA and IgG2b levels were higher in animals that were immunized intranasally. The demonstration that a high level of sIgA could be induced in the serum by intranasal administration of encapsulated antigen also confirmed the utility of this vaccine delivery system because of the importance of sIgA in mucosal immunity.

EXAMPLE 3

Intranasal administration of Pn14

The experiments described in Example 2 showed that encapsulated ovalbumin, a poor immunogen when administered intranasally in saline, was successful in inducing OVA-specific antibodies when it was administered intranasally in coated alginate microbeads. We then tried administering a therapeutically relevant soluble antigen to determine if intranasal administration of an encapsulated potential soluble vaccine candidate antigen was also effective at inducing an immune response. Alginate microbeads were prepared containing Pn14, a vaccine candidate molecule, as described in Example 1. BALB/c mice were primed and boosted as described in Example 2, bled at days 14 and 21, and PN14-specific antibody measured by ELISA as described in Example 4. Primary and secondary immune responses were obtained when 3 µg of encapsulated Pn14 was administered intranasally to mice. Moreover, Pn14 -specific IgG2b was detected as early as day 14, which was sooner than antibody for OVA was detected. The results of the testing on the sera taken at day 21 are presented in Table 3; the same grading scale described previously for Table 2 was used.

TABLE 3

Pn14-specific isotype secondary responses

| Pn14-specific Isotype | Antibody Level |
|---|---|
| IgM | + |
| IgG$_1$ | +++ |
| IgG$_{2a}$ | ++ |
| IgG$_{2b}$ | +++ |
| IgA | +++ |
| IgE | − |

Intranasal administration resulted in high titers of Pn14-specific antibodies in the serum, thereby confirming that intranasal administration of soluble vaccine molecules encapsulated in alginate microbeads provided an effective way of inducing an immune response.

The above experiments showed that effective antibody responses can be elicited when soluble antigens are encapsulated and released from alginate hydrogel matrix in a sustained release mechanism following intranasal administration. A minimal amount of antigen (as low as 3.5 µg of ovalbumin or 3 µg of Pn14) administered once intranasally was effective in inducing a primary immune response. A high serum level of IgG was detected as early as 14 days post primary immunization and the level was significantly increased after the secondary boosting. No IgE was detected in the serum when antigen was administered intranasally. The production of IgE is generally regarded as undesirable for a vaccination scheme, since IgE is thought to be an early indicator of the induction of tolerance, and antigen-specific IgE is likely to be involved in histamine-mediated anaphylactic shock that can occur with the repeated administration of an antigen.

EXAMPLE 4

Antigen specific ELISA

The titers of ovalbumin or Pn14-specified antibodies were determined by direct enzyme-linked immunosorbent assay (ELISA) in a 96-well microtiter plate format. For the OVA-specific antibody ELISA, microtiter plates (Corning, Corning, N.Y.) were coated with OVA (Sigma, St. Louis, Mo.) diluted in PBS at a concentration of 10 µg/ml, overnight at 4° C. For the Pn14-specific antibody ELISA, microtiter plates (Nunc, Denmark) were coated with Pn14 (Lederle-Praxis Biologicals, Rochester, N.Y.) diluted in PBS at a concentration of 4 µg/ml, overnight at 4° C.

Serum samples were serially diluted in sample diluent (PBS with 10% (v/v) normal goat serum obtained from Sigma), and 50 µl was added to duplicate wells. Non-immune normal mouse serum was used for a control. Plates were incubated for 1 hour at room temperature, then washed 4× with PBST (PBS, 0.05% Tween-20, v/v). Bound antibody of various subclasses was detected using subclass-specific horseradish peroxidase (HRP) conjugated antibodies directed against IgM, IgG1, IgG2a, IgG2b (Southern Biotech Associates Inc., Birmingham, Ala.), IgA (Organon Teknika-Cappel, Durham, N.C.) or IgE (Pharmingen, San Diego, Calif), or an antibody that recognizes all mouse heavy chains (Southern Biotech Associates Inc.), diluted 1:2000 in sample diluent. After a 30 minute incubation at room temperature, unbound HRP-antibody conjugates were washed away with PBST and 100 µl substrate (soluble TMB [tetra-methyl benzidene], Kirkegaard and Perry Laboratory, Gaithersburg, Md., USA) was added and allowed to develop for 10 minutes. The enzyme reaction was stopped by adding 100 µl of 1N H2SO$_4$ to each well. Absorbance was measured in each well using a 96-well microplate reader at 450 nm-560 nm.

EXAMPLE 5

Comparison of poly-cation coatings

Figure 1A:
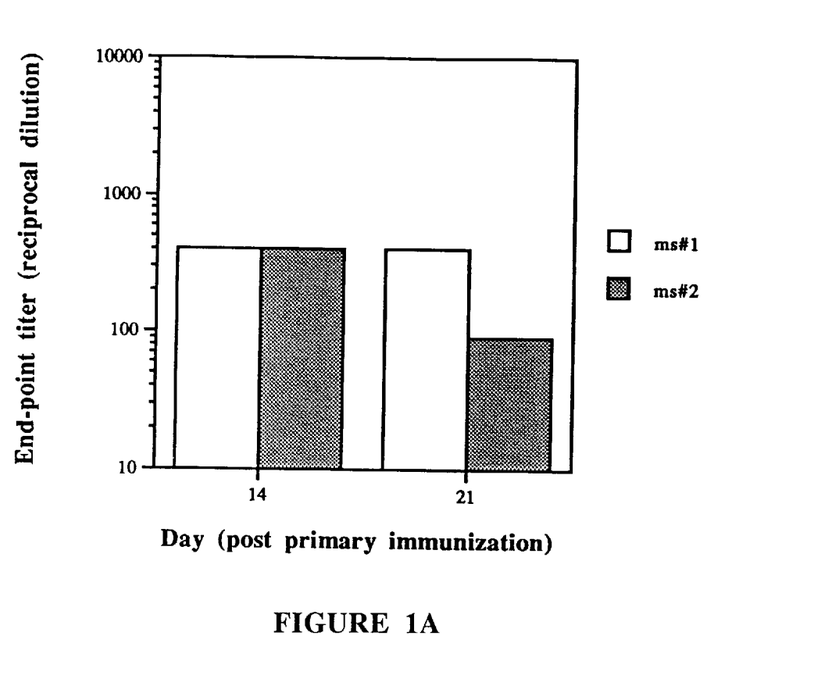
Figure 1B:
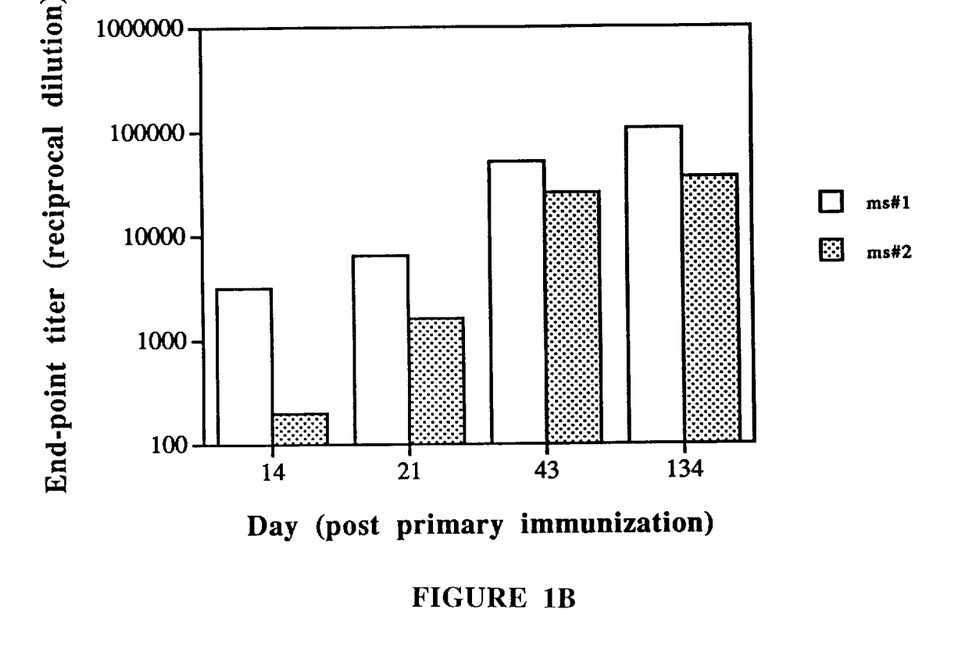

This experiment was designed to study the effect of different cation coatings on the duration of the antibody response to OVA. Antigen-containing microbeads were prepared substantially as described in Example 1 above, adding either poly-L-lysine, or polyhistidine (obtained from Sigma, St. Louis Mo.) to the cured, stirred solution of microbeads for a final concentration of 0.03%, or 0.01% (w/v), respectively. Mice were immunized substantially as described in Example 2, with a single administration of encapsulated OVA. Results are shown in FIG. 1.

OVA-specific antibody was detected in the serum over a period of 143 days when polyhistidine coated beads were administered; secondary and tertiary OVA antibody responses were observed with only a single administration of these OVA-containing beads. Poly-L-lysine coated alginate beads showed a shorter lived immune response, with the antibody titer leveling off at day 21. The results obtained suggested that a single dose vaccine administration is possible with this alginate microbead delivery system, and that the release profile can be controlled by stabilizing the alginate.

EXAMPLE 6

Levels of Immunoglobulin in Lung Secretions

Figure 2:
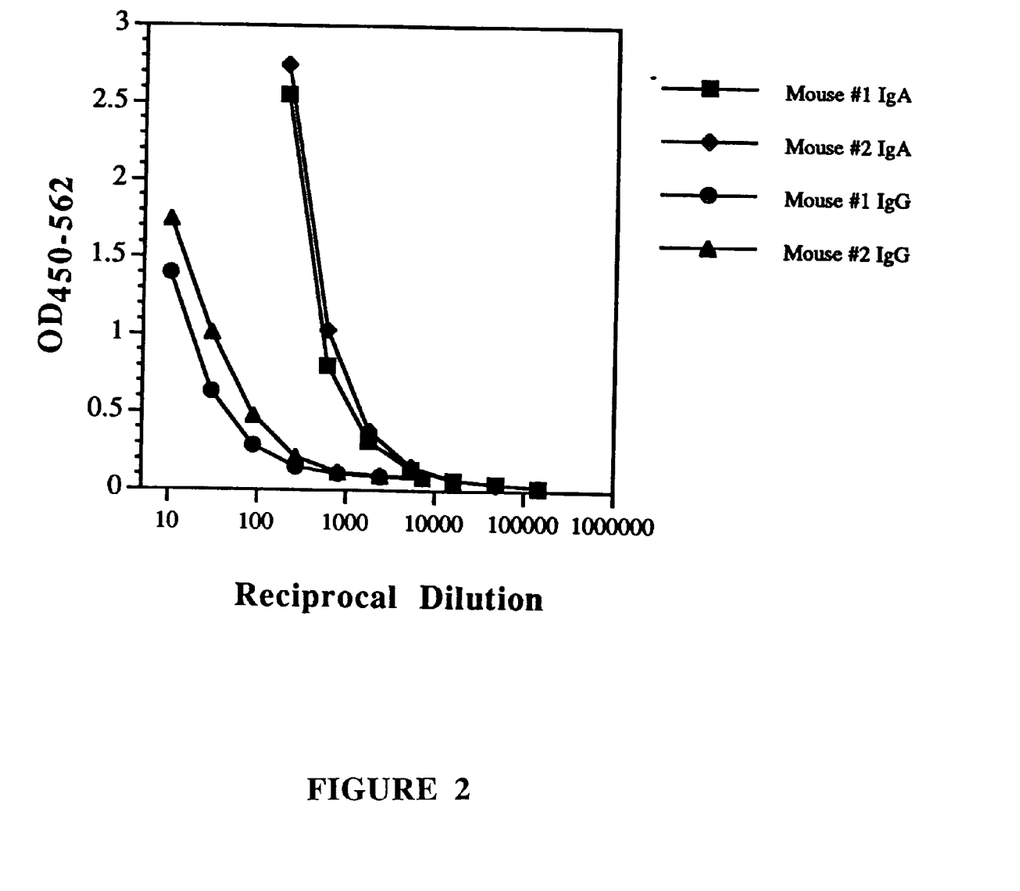
FIG. 2 demonstrates that mucosal immunoglobulin responses in mice immunized by intranasal instillation with encapsulated OVA are significantly greater that mice immunized by subcutaneous injection with encapsulated OVA, as described in Example 6.
Figure 3:
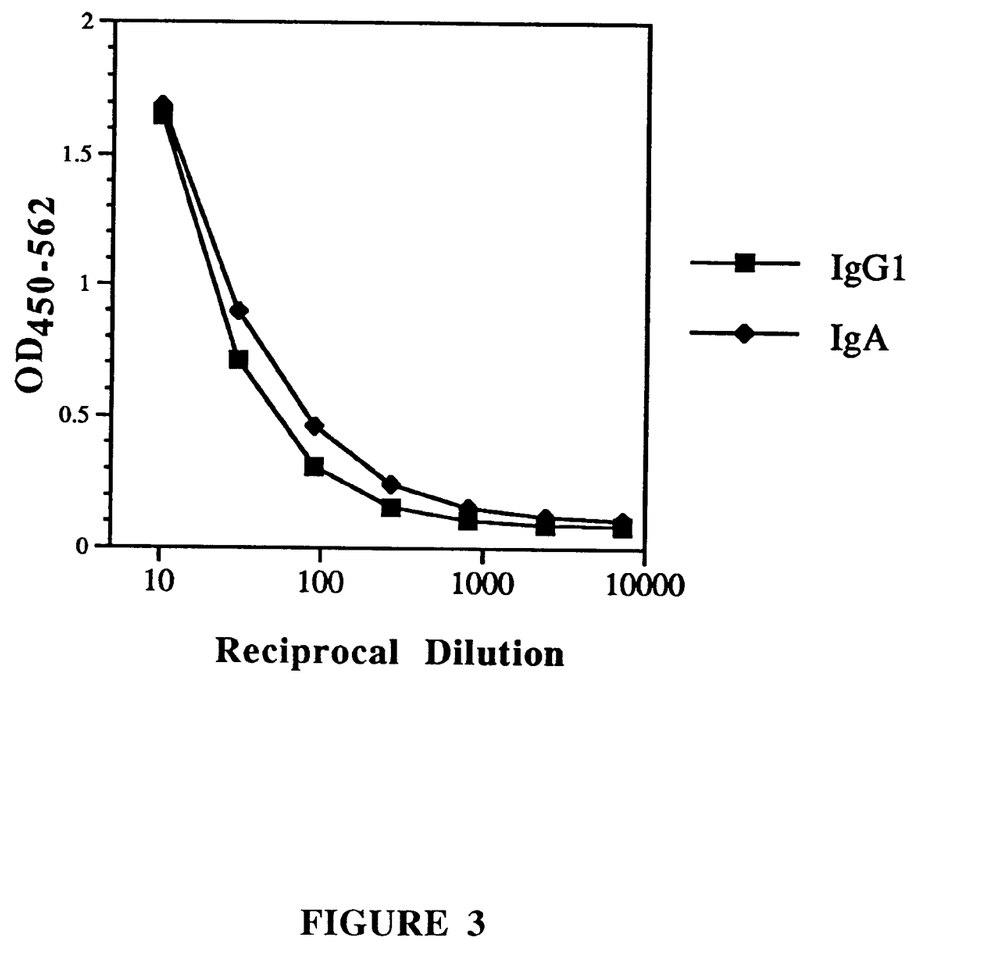
FIG. 3 presents results that demonstrate that the intranasal administration of Pn14 encapsulated in alginate microbeads, as described in Example 6, results in the development of a mucosal immune response as shown by the presence of antigen-specific IgG1 and IgA in bronchoalveolar lavage fluid. Mice immunized by subcutaneous injection of encapsulated Pn14 did not develop a detectable mucosal IGA immune response to this antigen.

The experiments described in Examples 2 and 3 showed that encapsulated antigen was successful in inducing antigen-specific serum antibodies, and indicated that the intranasal administration might be more effective at stimulating an IgA response. In another set of experiments, mice were immunized with antigen-containing (either OVA or PN14) alginate microbeads, substantially as described previously (at day 0 and day 14), either intranasally (3.6 $\mu$g of OVA; 3 $\mu$g Pn14) or subcutaneously (10 $\mu$g of OVA; 3 $\mu$g Pn14). At day 28, the mice were sacrificed and bronchoalveolar lavage (BAL) specimens were obtained and analyzed for the presence of antigen-specific IgA, $IgG_2a$ and $IgG_1$ by ELISA. Results are shown in FIGS. 2 and 3. Similar results were obtained with specimens taken at day 21.

High titers of IgA, $IgG_2a$ and $IgG_1$ were detected in mice immunized via the intranasal route, but not in the mice immunized subcutaneously. Moreover, similar results were observed when the mice were primed via intranasal administration and boosted either by subcutaneous or intraperitoneal injection. These results demonstrated that at least a priming immunization must occur by the intranasal route in order to generate an antigen-specific sIgA response in the mucosa of the respiratory tract.

EXAMPLE 7

Induction of Inflammatory Response in Lungs

Mice were immunized intranasally with OVA-containing microbeads as previously described. Cells were harvested from the lungs and analyzed for the types and numbers of cells present. After primary immunization, cellular infiltrates were composed of primarily macrophages at levels similar to those observed in unimmunized BALB/c mice. After secondary intranasal immunization, a subtle shift in the differential cell count was observed, with the most notable difference being the presence of eosinophils in the lung lavages of treated mice. These results demonstrated that the alginate microbeads did not induce a non-specific inflammatory response in the lungs, indicating that alginate beads are suitable for administration of antigen to the respiratory tract.

EXAMPLE 8

Localization of Alginate Beads

Phycoerythrin (PE)-labeled donkey IgG was encapsulated in alginate microbeads substantially as described in Example 1, and these microbeads were administered intranasally to mice. The animals were sacrificed 6 hours later, their lungs lavaged and the lavage fluid analyzed for the presence of IgG-containing microbeads. Less than 0.15% of the initial inoculated dose of the microbeads were recovered from the lungs, indicating that the majority of the alginate microbeads were localized in the nasopharynx rather than the lungs. These findings, in combination with the lack of an induction of a non-specific inflammatory response and the lack of induction of IgE, confirmed the utility of alginate microbeads for delivery of substances to the respiratory tract.

EXAMPLE 9

Release kinetics of coated alginate beads

In vitro release kinetics are analyzed by determining the amount of protein (determined by using an assay such as a BioRad protein assay, BioRad, Richmond, Calif., or by another suitable assay for quantitating protein) released over time from the beads. Other suitable assays can be used to quantitate the amount of antigen present, depending on the nature of the antigen. The release rate can be controlled by utilizing different coatings on the beads. In vitro experiments suggested that poly-L-lysine and polyarginine coated beads had similar release profiles, whereas polyhistidine coated beads provided longer, more sustained release of material. Beads that are less stable (i.e., uncoated beads), and hence have faster associated release kinetics, are also expected to be released quickly in vivo. A rapid release profile may make uncoated beads a desirable delivery agent for boosting an immune response. In vitro release kinetics will parallel the sustained release of material in vivo.

What is claimed is:

1. A composition to mucosal administration comprising an immunogenic amount of an antigen encapsulated in an alginate microbead having a mean diameter of from about 30 $\mu$m to about 50 $\mu$m, wherein the microbead is prepared by:

(a) providing a solution comprising an alginate and an antigen;

(b) forming microbeads comprising the alginate and the antigen by micronizing the alginate and antigen solution (c) curing the microbeads;

(d) stabilizing the cured microbeads by contacting the microbeads with a poly-cation; and (e) coating the stabilized microbeads with an additional coating of alginate.

2. The composition according to claim 1, further comprising an immunoregulatory molecule encapsulated in the alginate microbead.

3. The composition according to claim 2, wherein the immunoregulatory molecule is selected from the group consisting of GM-CSF, a fusion protein comprising GM-CSF and IL-3, CD40 ligand, IL-15, IL-16, antagonists of the interaction of CD30 and CD30 ligand, and combinations thereof.

4. The composition according to claim 1, wherein the antigen is a fusion protein comprising antigen and an immunoregulatory molecule.

5. The composition according to claim 4, wherein the immunoregulatory molecule is selected from the group consisting of GM-CSF, a fusion protein comprising GM-CSF and IL-3, CD40 ligand, IL-15, IL-16, and antagonists of the interaction of CD30 and CD30 ligand.

6. The composition according to claim 1, further comprising an immunogenic amount of one or more additional antigens encapsulated in the alginate microbead.

7. The composition according to claim 6, wherein at least one of the antigens is a fusion protein comprising the antigen and an immunoregulatory molecule.

8. The composition according to claim 7, wherein the immunoregulatory molecule is selected from the group consisting of GM-CSF, a fusion protein comprising GM-CSF and IL-3, CD40 ligand, IL-15, IL-16, and antagonists of the interaction of CD30 and CD30 ligand.

9. A method of eliciting an immune response to an antigen, comprising preparing a composition according to claim 1, and administering the composition to a mucosal surface of an individual in need of immunization.

10. The method of claim 9, wherein the composition further comprises an immunoregulatory molecule encapsulated in the alginate microbead.

11. The method of claim 9, wherein the antigen is a fusion protein comprising the antigen and an immunoregulatory molecule.

12. The method of claim 9, wherein the composition further comprises an immunogenic amount of one or more additional antigens encapsulated in the alginate microbead.

13. The method according to claim 12, wherein at least one of the antigens is a fusion protein comprising the antigen and an immunoregulatory molecule.

14. The method of claim 9, wherein the composition is administered intranasally.

15. The method of claim 10, wherein the composition is administered intranasally.

16. The method of claim 11, wherein the composition is administered intranasally.

17. The method of claim 12, wherein the composition is administered intranasally.

18. The method of claim 13, wherein the composition is administered intranasally.

\* \* \* \* \*